US00PP08444P

United States Patent [19]

Van Andel

[11] Patent Number: Plant 8,444

[45] Date of Patent: Nov. 2, 1993

[54] ALSTROEMERIA NAMED STAPRIPUR

[75] Inventor: Jacob Van Andel, Aalsmeer, Netherlands

[73] Assignee: Van Staaveren, B.V., Aalsmeer, Netherlands

[21] Appl. No.: 857,591

[22] Filed: Mar. 25, 1992

[51] Int. Cl.[5] ..... A01H 5/00

[52] U.S. Cl. ..... Plt./87.1

[58] Field of Search ..... Plt./87.1

*Primary Examiner*—James R. Feyrer

[57] ABSTRACT

A new and distinct variety of Alstroemeria plant particularly distinguished by its continuous and profuse production of medium sized flowers having a purple coloration. The inner petals are highlighted by a Lilac purple base portion. Each of the flowers comprising the bloom, carried on a stem of a length about 30 cm. This new variety of Alstroemeria plant is short stemmed and particularly suited for pot and garden.

1 Drawing Sheet

BACKGROUND OF THE NEW PLANT

My new Alstroemeria cultivar originating as a hybrid seedling developed by me by crossing seed parent No. 9318-1 and pollen parent No. 4469-1 from my collection of Alstroemeria maintained by me at my greenhouse in Aalsmeer, Holland and the present plant was selected by me from the several seedlings of the said cross-hybrid because of it being short stemmed and thus suited for a pot and garden which I considered to have good commercial merit. The seed parent, 9318-1, has not been patented and has not been released into commerce. The pollen parent, 4489-1 is also unpatented and has never been released into commerce. At the moment, the pollen parent does not exist. This selected seedling was propagated by the division of root stocks and such propagation was carried on through several successive generations at Aalsmeer which demonstrated that the novel characteristics of this variety would hold true from generation to generation and its homogeneity could thereby be assured for propagation on a commercial scale.

DESCRIPTION OF THE DRAWING

This new Alstroemeria cultivar is illustrated by the accompanying photographic drawing which shows face views of a number of the flowers comprising an umbel cluster, the color rendation being as nearly true to those specified herein as is possible to obtain by conventional photographic procedures.

DESCRIPTION OF THE NEW PLANT

The following is a detailed description of my new Alstroemeria cultivar as observed in September 1980 from flowers grown in greenhouse at Aalsmeer, Holland, the color designations being according to the R.H.S. Colour Chart of the Royal Horticultural Society of London, England.

THE PLANT

Origin: Seedling.

Parentage:

*Seed parent.*—9318-1 (unpatented).

*Pollen parent.*—4469-1 (unpatented).

Classification: Alstroemeria hybrid.

Form: Bush.

Height: Approximately 30 cm.

Growth habit: This plant is fast growing with vigorous, upright stems of good strength.

Foliage:

*Quantity.*—Abundant.

*Leaf size.*—12×1.5 cm.

*Leaf shape.*—Elliptical/Lancelets with straight margins.

*Texture.*—Glossy.

*Color.*—Upper side — RHS 141-B. Under side — RHS 137-B.

Rizomes:

*Color.*—White.

*Size.*—Varies depending upon the season.

THE BUD

Size:

*Diameter.*—About 1-1.5 cm.

*Length.*—About 2.5-3 cm.

Form: Pear-shaped.

INFLORESCENCE

Blooming habit: Profusely continuous.

Size of flower: Medium.

*Diameter.*—About 4-5 cm.

*Depth.*—About 4-5 cm.

Borne: Singly on a stem.

Shape: Cup-shaped when bloom first opens and when bloom matures.

Petalage:

*Number of petals.*—Six.

Arrangement: Two concentric circles of three petals each.

Texture: Soft.

Appearance: Satiny.

Color:

*Outer petals.*—Body — Purple 71B with a base portion of Purple 71C. Reverse side — Purple 71B.

*Inside petals.*—Body — Purple 71B with a base portion Lilac Purple 70B. Reverse side — Purple 71B. The two inner, upper petals overlap, and each contains a conspicuous central band, RHS 155D in color, fused across the central portion and extending side to side to each margin. All of the petals, both inner and outer are covered end to end with short, dark pencil stripes extending longitudinally of the petals.

Flower stem:

*Length.*—Approximately 3 to 4 cm.

*Character.*—Erect.

*Color.*—Green.

Discoloration after full bloom: None.

Persistence: The flower petals stay on the stem for more than two weeks after becoming fully open.

Lasting quality: On the plant, about 21 days.

THE REPRODUCTIVE ORGANS

Stamens:

*Number.*—Six.

*Arrangement.*—One opposite each petal.

*Anthers.*—Size: 0.8 cm. Color: Undehisced anthers: light green, Dehisced anthers: gray/brown.

*Filaments.*—Length: About 3-4 cm. Color: Pink.

*Pollen.*—Color: Grey.

Pistils:

*Number.*—One.

*Style.*—Length: About 4-5 cm. Color: Pink/purple.

*Stigma.*—Color: Purple red.

THE FRUIT

Fertility: The fruit is fertile.

Shape: Round.

Color: At maturity brown.

I claim:

1. The new and distinctive Alstroemeria cultivar, substantially as herein shown and described, characterized by the generally purple coloration of its medium blooms and distinguished in particular by all of the petals, both inner and outer, having dark pencil stripes extending longitudinally of the petals and a Lilac purple coloring of the base portion of the inner petals.

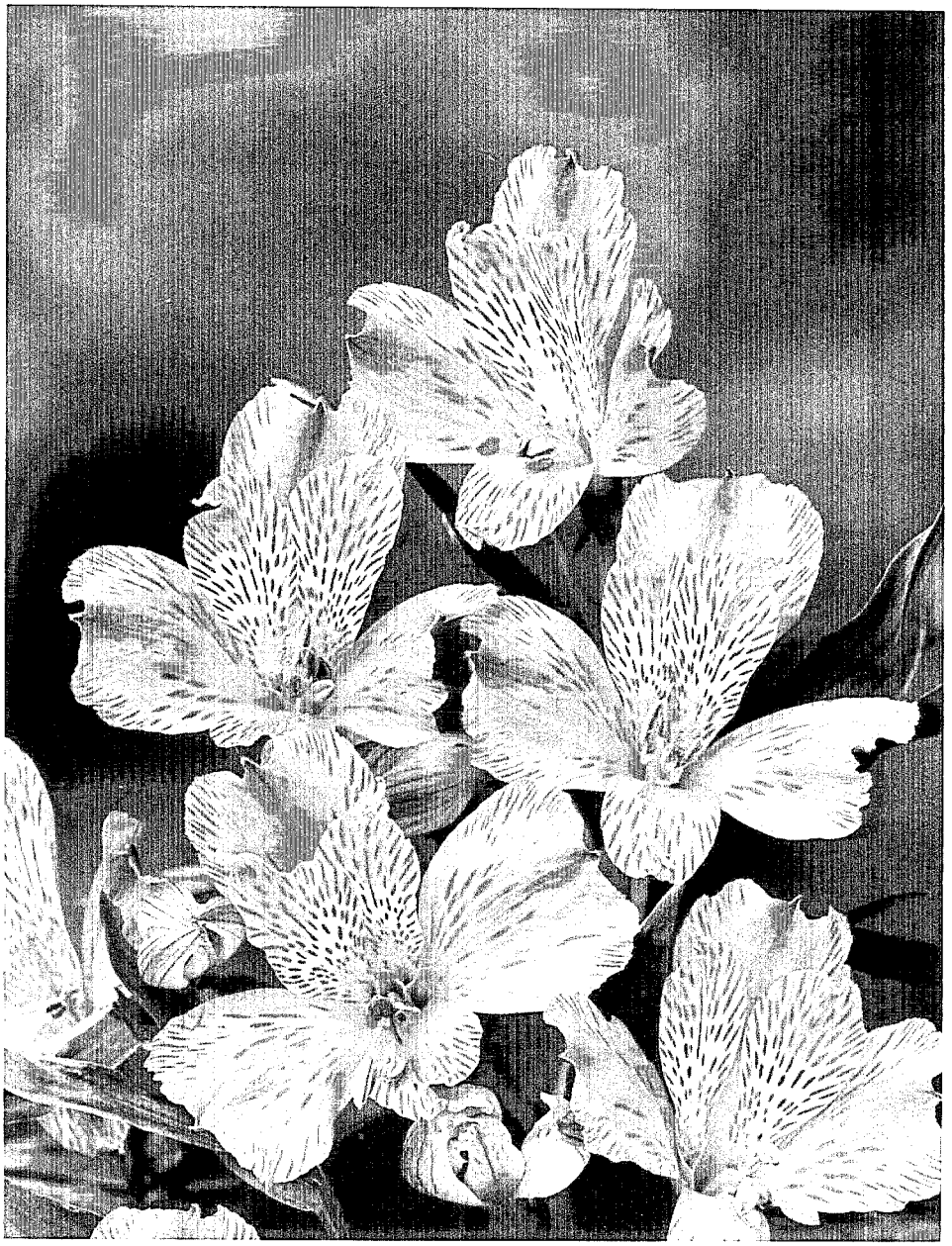

* * * * *